(12) United States Patent
Fujita et al.

(10) Patent No.: US 9,702,834 B2
(45) Date of Patent: Jul. 11, 2017

(54) INSPECTION METHOD FOR BEARING PART AND INSPECTION APPARATUS FOR BEARING PART

(71) Applicants: Takumi Fujita, Kuwana (JP); Kazuhiro Yagita, Kuwana (JP); Toshihiko Sasaki, Kanazawa (JP); Youichi Maruyama, Hamamatsu (JP)

(72) Inventors: Takumi Fujita, Kuwana (JP); Kazuhiro Yagita, Kuwana (JP); Toshihiko Sasaki, Kanazawa (JP); Youichi Maruyama, Hamamatsu (JP)

(73) Assignee: NTN CORPORATION, Osaka (JP)

(*) Notice: Subject to any disclaimer, the term of this patent is extended or adjusted under 35 U.S.C. 154(b) by 143 days.

(21) Appl. No.: 14/412,629

(22) PCT Filed: Jul. 2, 2013

(86) PCT No.: PCT/JP2013/068131
§ 371 (c)(1),
(2) Date: Jan. 2, 2015

(87) PCT Pub. No.: WO2014/007246
PCT Pub. Date: Jan. 9, 2014

(65) Prior Publication Data
US 2015/0146857 A1    May 28, 2015

(30) Foreign Application Priority Data
Jul. 4, 2012 (JP) .................................. 2012-150642

(51) Int. Cl.
*G01N 23/207* (2006.01)
*G01N 23/20* (2006.01)

(52) U.S. Cl.
CPC .......... *G01N 23/207* (2013.01); *G01N 23/20* (2013.01); *G01N 2223/624* (2013.01); *G01N 2223/632* (2013.01)

(58) Field of Classification Search
CPC ................. G01N 23/20; G01N 23/207; G01N 2223/0566; G01N 2223/607;
(Continued)

(56) References Cited

U.S. PATENT DOCUMENTS 4,404,682 A * 9/1983 Hayashi ................. G01N 23/20
378/72
4,709,383 A * 11/1987 Goto ...................... G01N 23/20
378/71
(Continued)

FOREIGN PATENT DOCUMENTS

CN    102721712 A    10/2012
GB    2083215 A    3/1982
(Continued)

OTHER PUBLICATIONS

N. Oguma, "Prediction of Residual Fatigue Life of Bearings—Part 1: Application of X-Ray Diffraction Method", 2002, KOYO Engineering Journal, English Edition No. 161E.*
(Continued)

*Primary Examiner* — David J Makiya
*Assistant Examiner* — Soorena Kefayati
(74) *Attorney, Agent, or Firm* — McDermott Will & Emery LLP

(57) ABSTRACT

An inspection method for a bearing part includes the steps of: emitting X-rays onto a fatigued portion of a bearing part to be inspected; detecting annular diffracted X-rays (X-ray diffraction ring) diffracted by the fatigued portion; and
(Continued)

estimating a use condition of the bearing part to be inspected, based on the detected annular diffracted X-rays (X-ray diffraction ring).

3 Claims, 3 Drawing Sheets

(58) Field of Classification Search
CPC ....... G01N 2223/624; G01N 2223/632; G01N 2223/634
See application file for complete search history.

(56) References Cited

U.S. PATENT DOCUMENTS

| | | | | |
|---|---|---|---|---|
| 7,623,973 | B1* | 11/2009 | Wang | G01M 5/0033 702/185 |
| 7,918,141 | B1* | 4/2011 | Sathish | F01D 5/286 73/105 |
| 2010/0239068 | A1* | 9/2010 | Belassel | G01N 3/32 378/72 |
| 2011/0241661 | A1* | 10/2011 | Nomura | G01N 27/9046 324/239 |

FOREIGN PATENT DOCUMENTS

| | | | |
|---|---|---|---|
| JP | 2005-241308 A | | 9/2005 |
| JP | 2009041993 A | * | 2/2009 |
| JP | 2011-27550 A | | 2/2011 |
| JP | 2011-69684 A | | 4/2011 |

OTHER PUBLICATIONS

International Search Report PCT/JP2013/068131 filed Aug. 27, 2013 with English translation.
Noriyasu Oguma, "Prediction of Residual Fatigue Life of Bearings, Part 1: Application of X-ray Diffraction Method", KOYO Engineering Journal, Apr. 2002, No. 161, pp. 26-31 with partial English translation.
Junzo Okamoto, "Dynamic Load Capacity of Rolling Bearing and Roller Bearing: Detailed Explanation of Lundberg-Palmgren Theory", Machine Element Course by Chiba University, Faculty of Engineering, Department of Mechanical Engineering, 1988, pp. 25-34 with partial English translation.
Noriyuki Tsushima et al., "Application of X-Ray Measurement to Bearing Failure Analysis", Bearing Engineer No. 49, 1984, pp. 25-34 with partial English translation.
Supplementary European Search Report EP Application No. 13813631.2 dated Jan. 29, 2016.
Notice of the First Office Action Chinese Patent Application No. 201380035589.2 dated Jul. 14, 2016 with full English translation.

* cited by examiner

INSPECTION METHOD FOR BEARING PART AND INSPECTION APPARATUS FOR BEARING PART

CROSS-REFERENCE TO RELATED APPLICATION

This application is the U.S. National Phase of PCT/JP2013/068131 filed Jul. 2, 2013 which claims priority from Japanese Patent Application No. 2012-150642 filed Jul. 4, 2012. The subject matter of each is incorporated herein by reference in entirety.

TECHNICAL FIELD

The present invention relates to an inspection method for a bearing part and an inspection apparatus for a bearing part. More particularly, the present invention relates to an inspection method for a bearing part and an inspection apparatus for a bearing part that allow high-precision inspection of a bearing part.

BACKGROUND ART

It is known that the life of a rolling bearing depends on a load applied to the bearing, a lubrication condition, a material that forms a bearing part, and the like. The life of the rolling bearing can be calculated by using a life calculation equation created in consideration of the aforementioned load, lubrication condition, material and the like (refer to, for example, "Dynamic Load Capacity of Rolling Bearing and Roller Bearing: Detailed Explanation of Lundberg-Palmgren Theory" (NPD 1)). This calculation equation is used to estimate how long the rolling bearing can be used when the rolling bearing is used under a certain condition or to estimate under what condition the rolling bearing should be used in order to prevent the rolling bearing from being broken during the requested time.

Generally, the rolling bearing is used under a use condition set based on the life calculation equation. Therefore, as long as the rolling bearing is used under a normal condition, the life of the rolling bearing does not matter. In the market, however, there often arises a situation in which the life of the rolling bearing becomes an issue. One cause for this is considered to be that the actual use condition of the rolling bearing is different from the scheduled condition. In order to deal with such a situation, there has been proposed a method for analyzing an actually used rolling bearing and estimating the remaining life of the rolling bearing (refer to, for example, Noriyuki Tsushima et al., Bearing Engineer 49, 1984, 25-34(NPD 2)). This method is a method using the fact that a result of stress measurement (stress, half-value width, amount of remaining austenite) with X-ray diffraction has a relation with the rolling time (operating time) of the rolling bearing.

CITATION LIST

Non Patent Document

NPD 1: Junzo Okamoto, "Dynamic Load Capacity of Rolling Bearing and Roller Bearing: Detailed Explanation of Lundberg-Palmgren Theory", Machine Element Course by Chiba University, Faculty of Engineering, Department of Mechanical Engineering, 1988NPD 2: Noriyuki Tsushima et al., Bearing Engineer, 49, 1984, 25-34

SUMMARY OF INVENTION

Technical Problem

However, this method uses the relation between the stress measurement result and the rolling time under a particular rolling condition. Therefore, this method has had such a problem that this method can be applied only to a rolling bearing used under a condition close to that condition.

In order to estimate the remaining life of the rolling bearing under an arbitrary rolling condition, a method for estimating a use condition of the rolling bearing by using some kind of means, and estimating how long the rolling bearing has been used under that condition (the number of loading) is required. When there is no disturbance factor such as contamination (debris contamination) of lubricating oil, the main factors dominating the life of the rolling bearing are a load and an oil film parameter. Therefore, in order to estimate the remaining life, it is necessary to estimate the three conditions, i.e., the aforementioned two conditions and the number of loading. Even with conventional X-ray diffraction, the three analysis results of the stress, the half-value width and the amount of remaining austenite are obtained. However, there has been such a problem that it is difficult to estimate the use condition (the number of loading, the load and the oil film parameter) of the rolling bearing with high precision based on these analysis results.

The present invention has been made to solve the aforementioned problems, and an object of the present invention is to provide an inspection method and an inspection apparatus for a bearing part that allow high-precision estimation of a use condition of a rolling bearing.

Solution to Problem

An inspection method for a bearing part according to the present invention includes the steps of: emitting X-rays onto a fatigued portion of a bearing part to be inspected; detecting annular diffracted X-rays diffracted by the fatigued portion; and estimating a use condition of the bearing part to be inspected, based on the detected annular diffracted X-rays.

In the case of causing the X-rays to enter the bearing part at a prescribed incidence angle, the X-rays are diffracted to form a conical surface, as long as the steel forming the bearing part is a polycrystalline body formed of many crystals having random orientations. Even when the X-rays are diffracted as described above, only the diffracted X-rays corresponding to one direction, of the diffracted X-rays forming the aforementioned conical surface, are detected by a detector in stress analysis for the bearing part with conventional X-ray diffraction. Then, the incidence angle is changed and the diffracted X-rays are similarly detected again, and the stress on a surface of the bearing part is calculated based on these. As described above, in the analysis method with conventional X-ray diffraction, only the diffracted X-rays corresponding to one direction, of the diffracted X-rays forming the conical surface, are detected and analyzed. Therefore, an amount of information obtained in one measurement is limited and an extremely large number of measurements are required to estimate the use condition of the bearing part with high precision. Therefore, it is considered to be substantially impossible to use the conventional X-ray diffraction method to estimate the use condition of the bearing part with high precision.

In contrast, in the inspection method for the bearing part of the present invention, a detector having a planar detection unit is arranged at a position intersecting with all of the diffracted X-rays forming the aforementioned conical surface, and this detector detects the annular diffracted X-rays (X-ray diffraction ring) corresponding to an annular region formed by intersection of a plane including the detection unit and the aforementioned conical surface. This X-ray diffraction ring includes information about all of the diffracted X-rays forming the aforementioned conical surface. Therefore, the amount of information obtained in one measurement is significantly larger than that in the aforementioned conventional method. As a result, the use condition of the bearing part can be estimated with high precision. As described above, according to the inspection method for the bearing part of the present invention, the use condition of a rolling bearing can be estimated with high precision.

In the aforementioned inspection method for a bearing part, the step of estimating a use condition of the bearing part to be inspected may include the steps of: deriving use condition elements including normal stress at the fatigued portion, shear stress at the fatigued portion, a relation between a central angle and an intensity of the annular diffracted X-rays, and a half-value width of a peak obtained in accordance with the central angle of the annular diffracted X-rays, based on the annular diffracted X-rays detected in the step of detecting annular diffracted X-rays; and calculating the use condition of the bearing part to be inspected, based on at least one of the derived use condition elements.

The normal stress at the fatigued portion, the shear stress at the fatigued portion, the relation between the central angle and the intensity of the diffracted X-rays, and the half-value width of the peak obtained in accordance with the central angle of the annular diffracted X-rays have a strong correlation with the use condition of the rolling bearing. Therefore, by calculating the use condition based on these derived use condition elements, the use condition of the rolling bearing can be estimated with higher precision.

The aforementioned inspection method for a bearing part may further include the step of evaluating a remaining life of the bearing part to be inspected, based on the use condition of the bearing part to be inspected which was calculated in the step of estimating a use condition of the bearing part to be inspected.

Thus, it is possible to obtain information about the time for replacement of the bearing, which is important for the user of the rolling bearing.

In the aforementioned inspection method for a bearing part, the use condition elements may further include an amount of austenite remaining in the fatigued portion. There is also a strong correlation between the amount of austenite remaining in the fatigued portion and the use condition of the rolling bearing. Therefore, by calculating the use condition of the rolling bearing based on the amount of remaining austenite, the use condition of the rolling bearing can be estimated with higher precision.

In the aforementioned inspection method for a bearing part, in the step of estimating a use condition, the number of loading of stress applied to the fatigued portion of the bearing part to be inspected, a load applied to the fatigued portion, and an oil film parameter at the fatigued portion may be calculated based on a relation of at least any one of the normal stress at the fatigued portion, the shear stress at the fatigued portion, the amount of remaining austenite, the relation between the central angle and the intensity of the annular diffracted X-rays, and the half-value width of the peak obtained in accordance with the central angle of the annular diffracted X-rays, about the preliminarily researched bearing part, with the number of loading of stress applied to the fatigued portion of the bearing part, the load applied to the fatigued portion of the bearing part, and the oil film parameter at the fatigued portion of the bearing part.

As described above, the relation between the use condition elements and the actual use condition (the number of loading, the load and the oil film parameter) is preliminarily researched, and the use condition is derived from the use condition elements obtained by analysis of the bearing part to be inspected. Therefore, the use condition of the rolling bearing can be estimated with high precision.

In the aforementioned inspection method for a bearing part, in the step of estimating a use condition, each of the number of loading of stress applied to the fatigued portion of the bearing part to be inspected, the load applied to the fatigued portion or the bearing part to be inspected, and the oil film parameter at the fatigued portion of the bearing part to be inspected may be statistically calculated to take into consideration a relation of each of the normal stress at the fatigued portion, the shear stress at the fatigued portion, the amount of remaining austenite, the relation between the central angle and the intensity of the annular diffracted X-rays, and the half-value width of the peak obtained in accordance with the central angle of the annular diffracted X-rays, about the preliminarily researched bearing part, with all of the number of loading of stress applied to the fatigued portion of the bearing part, the load applied to the fatigued portion of the bearing part, and the oil film parameter at the fatigued portion of the bearing part.

As described above, each use condition is not determined based on the relation with one use condition element but calculated as the most likely value based on the relation with a plurality of use condition elements. Therefore, the use condition of the rolling bearing can be estimated with higher precision.

An inspection apparatus for a bearing part according to the present invention includes: an irradiation unit for emitting X-rays onto a bearing part to be inspected; a detector for detecting annular X-rays diffracted by the bearing part to be inspected; and a computation unit connected to the detector, for calculating a use condition of the bearing part to be inspected, based on the annular X-rays detected by the detector.

With such a structure, according to the inspection apparatus for the bearing part of the present invention, the aforementioned inspection method for the bearing part of the present invention can be easily performed.

The aforementioned inspection apparatus for a bearing part is preferably portable. Thus, inspection can be easily conducted at a place where the bearing part is used or near that place.

Advantageous Effects of Invention

As is clear from the foregoing description, according to the inspection method for the bearing part and the inspection apparatus for the bearing part of the present invention, the use condition of the rolling bearing can be estimated with high precision.

DESCRIPTION OF EMBODIMENTS

Figure 1:
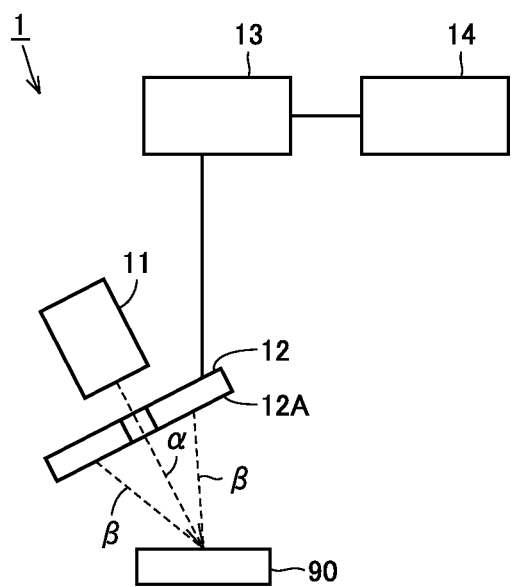
FIG. 1 is a schematic view showing a configuration of an inspection apparatus for a bearing part.

An embodiment of the present invention will be described hereinafter with reference to the drawings. In the following drawings, the same or corresponding portions are denoted by the same reference numerals, and description thereof will not be repeated.

As shown in FIG. 1, an inspection apparatus 1 for a bearing part according to one embodiment of the present invention includes an irradiation unit 11 for emitting X-rays onto a bearing part 90 to be inspected, a detector 12 for detecting annular X-rays diffracted by bearing part 90 to be inspected, a computation unit 13 connected to detector 12, for calculating a use condition of bearing part 90 to be inspected, based on the annular X-rays detected by detector 12, and a display unit 14 connected to computation unit 13, for displaying a result of computation by computation unit 13.

Irradiation unit 11 includes an X-ray tube placed to be capable of facing bearing part 90 to be inspected. Detector 12 includes a hole formed in a central portion to allow the X-rays emitted from the irradiation unit to pass through, and a planar detection unit 12A that can face bearing part 90 to be inspected. Computation unit 13 calculates the use condition of bearing part 90 to be inspected, based on a database prestored in a memory unit (not shown) and the data of the annular X-rays detected by detector 12. The calculated use condition of bearing part 90 to be inspected is displayed on display unit 14.

In addition, inspection apparatus 1 may be portable. The "portable" inspection apparatus herein does not mean that inspection apparatus 1 is installed in a certain place and bearing part 90 to be inspected needs to be conveyed to that place to conduct inspection. The "portable" inspection apparatus herein means that inspection apparatus 1 is movable and can be conveyed to a place where bearing part 90 to be inspected is used or near that place, to conduct inspection. In order to make inspection apparatus 1 movable, it is necessary to configure inspection apparatus 1 in a lightweight and compact manner. By using an X-ray CCD as detection unit 12A of detector 12, providing the X-ray tube of irradiation unit 11 and detector 12 within a housing, and providing computation unit 13 and display unit 14 as small-sized computer devices (such as personal computers), inspection apparatus 1 as a whole can be made compact. By making inspection apparatus 1 as a whole compact, the X-ray tube of irradiation unit 11 and detector 12 can be brought close to bearing part 90 to be inspected. As a result, output of the X-ray tube can be reduced, and thus, it also becomes possible to change cooling of the tube from water cooling to air cooling, and inspection apparatus 1 can be made more compact and lightweight.

Figure 2:
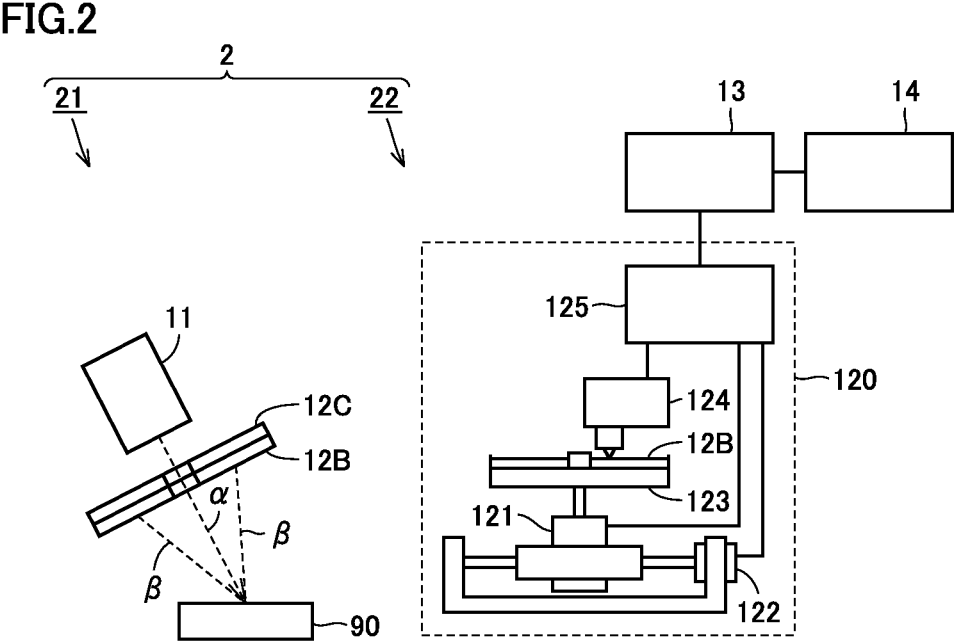
FIG. 2 is a schematic view showing another configuration of the inspection apparatus for the bearing part.

An inspection apparatus 2 can also be used in which an imaging plate 12B placed on a table 12C as shown in FIG. 2 is used instead of detection unit 12A in inspection apparatus 1 shown in FIG. 1 above. Referring to FIG. 2, inspection apparatus 2 includes a first device 21 for emitting X-rays and receiving diffracted X-rays, and a second device 22 for reading an image of the diffracted X-rays, calculating a use condition, and displaying a result of calculation. First device 21 has a structure basically similar to the structures of irradiation unit 11 and detector 12 in inspection apparatus 1 shown in FIG. 1 above. However, instead of detector 12 in inspection apparatus 1, first device 21 includes table 12C and imaging plate 12B placed on table 12C in a freely detachable manner to face bearing part 90 to be inspected. On the other hand, second device 22 includes a table 123 for detachably holding imaging plate 12B, a first motor 121 connected to table 123, for rotating table 123, and a second motor 122 connected to first motor 121, for moving first motor 121 two-dimensionally (e.g., moving first motor 121 in the X-Y direction). These first motor 121 and second motor 122 allow imaging plate 12B held by table 123 to rotate and move two-dimensionally. Furthermore, second device 22 includes a laser beam irradiation device 124 for emitting laser beams onto imaging plate 12B held by table 123 and receiving the light reflected from imaging plate 12B, and a calculation circuit 125 connected to laser beam irradiation device 124, first motor 121 and second motor 122, for calculating the data of annular diffracted X-rays based on signals from these components. First motor 121, second motor 122, table 123, laser beam irradiation device 124, and calculation circuit 125 described above constitute a read unit 120 for reading the data of the annular diffracted X-rays from imaging plate 12B. In addition, read unit 120, imaging plate 12B and table 12C function as an X-ray detector.

Second device 22 further includes computation unit 13 connected to calculation circuit 125 in read unit 120, and display unit 14 connected to the computation unit.

Computation unit 13 and display unit 14 have configurations similar to those in inspection apparatus 1 described above. Inspection apparatus 2 includes first device 21 and second device 22 as described above, and first device 21 and second device 22 may be portable in combination or independently.

Next, an inspection method for a bearing part using inspection apparatus 1 or 2 described above will be described. Referring to FIG. 2, a step of preparing bearing part 90 to be inspected and emitting X-rays onto a fatigued portion of this bearing part 90 to be inspected (S10) is first performed. In this step (S10), referring to FIGS. 1 and 2, bearing part 90 to be inspected is set at a prescribed position and the X-rays are emitted from irradiation unit 11 onto bearing part 90 to be inspected. At this time, as shown in FIGS. 1 and 2, the X-rays are emitted along an arrow a to enter bearing part 90 to be inspected at a prescribed incidence angle.

Figure 3:
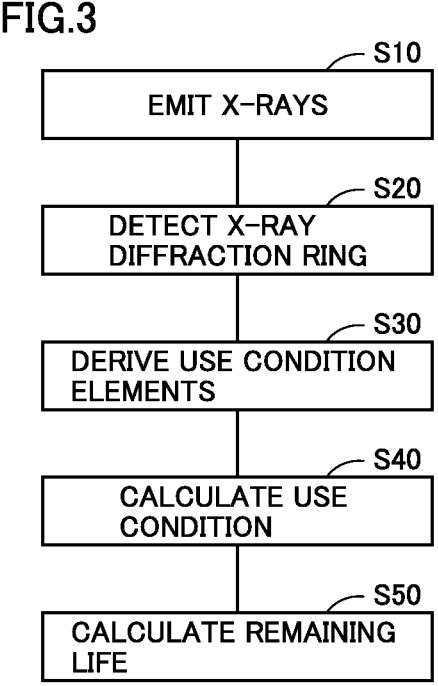
FIG. 3 is a flowchart schematically showing a procedure of an inspection method for the bearing part.

Next, referring to FIG. 3, a step of detecting an X-ray diffraction ring (S20) is performed. In this step (S20), as shown in FIGS. 1 and 2, the X-rays having entered bearing part 90 to be inspected along arrow α are diffracted to form a conical surface β, and reach detection unit 12A or imaging plate 12B. Then, in detection unit 12A which is, for example, an X-ray CCD, annular diffracted X-rays (X-ray diffraction ring) are detected based on a signal of the intensity corresponding to the intensity of the X-rays output by each pixel.

In inspection apparatus 2, an image of the X-ray diffraction ring is formed on imaging plate 12B. Therefore, imaging plate 12B is set in read unit 120 and the X-ray diffraction ring is detected based on the laser beam irradiation position (rotation angle and movement position) and a signal corresponding to the intensity of the reflected light in imaging plate 12B.

More specifically, although the image of the annular diffracted X-rays is formed on imaging plate 12B, the annular diffracted X-rays cannot be detected as-is. Therefore, imaging plate 12B is detached from table 12C and is set on table 123 of read unit 120. Imaging plate 12B held by table 123 receives the irradiation of the laser beams from laser beam irradiation device 124, while being rotated and moved by first motor 121 and second motor 122. As a result, the signal corresponding to the intensity of the light reflected from imaging plate 12B is output from laser beam irradiation device 124. Namely, stimulable luminescence having an amount of light corresponding to the intensity of the X-rays is generated from a site where the image of the diffracted X-rays is formed, and thus, the intensity of the signal corresponding to the intensity of the reflected light represents the intensity of the diffracted X-rays. In addition, the rotation position and the movement position of imaging plate 12B can be detected based on signals output from encoders in first motor 121 and second motor 122. Therefore, by inputting the signal output by laser beam irradiation device 124 and the signals output from the encoders in first motor 121 and second motor 122 into calculation circuit 125 and performing data processing, the annular diffracted X-rays can be detected similarly to the case of the X-ray CCD.

Together with imaging plate 12B and table 12C, read unit 120 may be provided within one housing, and creation of the image of the annular diffracted X-rays on imaging plate 12B with X-ray irradiation and detection (reading) of the annular diffracted X-rays by read unit 120 may be performed continuously.

Next, referring to FIG. 3, a step of deriving use condition elements (S30) is performed. In this step (S30), data relevant to a condition (use condition) under which bearing part 90 to be inspected has been used, e.g., data (use condition elements) such as normal stress at the fatigued portion of bearing part 90 to be inspected, shear stress at the fatigued portion, a relation between a central angle and the intensity of the annular diffracted X-rays, a half-value width of a peak obtained in accordance with the central angle of the annular diffracted X-rays, and an amount of remaining austenite, is obtained based on the X-ray diffraction ring detected in the aforementioned step (S20).

Next, referring to FIG. 3, a step of calculating a use condition (S40) is performed. In this step (S40), the use condition of bearing part 90 to be inspected is calculated based on the use condition elements obtained in the aforementioned step (S30). Specifically, the use condition can be estimated as described below, for example. Estimation (calculation) of the use condition is performed in computation unit 13 connected to detector 12 (see FIGS. 1 and 2).

The inventors of the present invention researched X-ray diffraction rings for the rolling bearing used under different use conditions. As a result of their research, the inventors of the present invention found that the compressive stress which is the normal stress, the intensity distribution with respect to the central angle of the X-ray diffraction ring, and the distribution of the half-value width change depending on the use condition of the rolling bearing. Therefore, by preliminarily researching a relation between each of the aforementioned use condition elements and the actual use condition (the number of loading, the load and the oil film parameter) based on the X-ray diffraction ring including a large amount of data, it is possible to estimate, based on this relation, the actual use condition when a prescribed use condition element is derived for bearing part 90 to be inspected.

Figure 4:
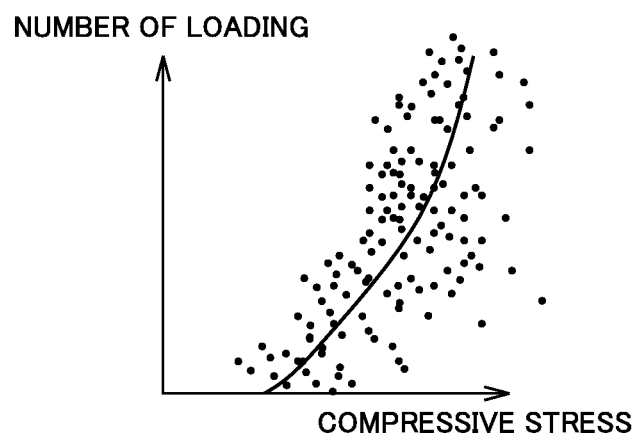
FIG. 4 is a diagram showing one example of a relation between the stress and the number of loading at a fatigued portion of the bearing part researched preliminarily.
Figure 5:
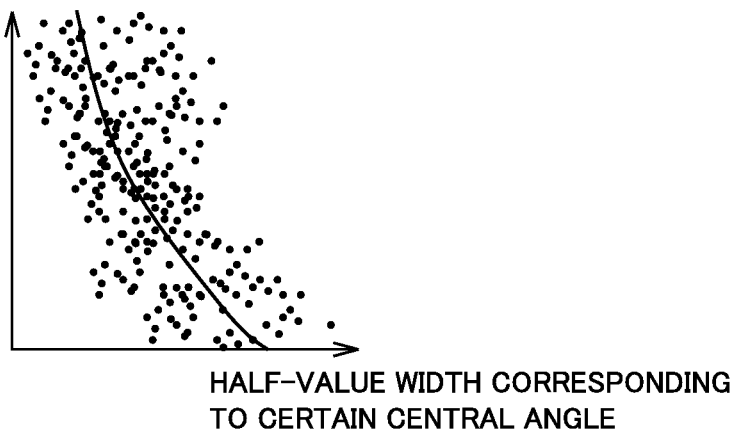
FIG. 5 is a diagram showing one example of a relation between the half-value width of diffracted X-rays corresponding to a certain central angle and the number of loading that are researched preliminarily.
Figure 6:
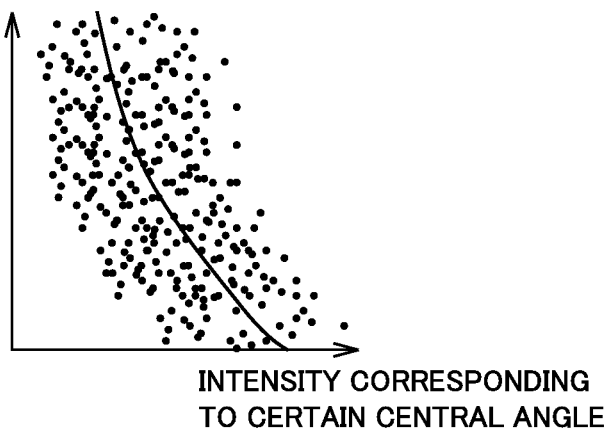
FIG. 6 is a diagram showing one example of a relation between the intensity of diffracted X-rays corresponding to a certain central angle and the number of loading that are researched preliminarily.

It is now assumed that relations (databases) shown in FIGS. 4 to 6 are obtained as a result of research of diffraction X-ray rings at fatigued portions of bearing parts that form various types of rolling bearings used under various use conditions. In FIGS. 4 to 6, the vertical axes indicate the number of actual loading, and the horizontal axes indicate the stress (compressive stress), the half-value width corresponding to a certain central angle, and the peak intensity corresponding to a certain central angle, respectively, which are obtained as a result of analysis of the bearing part at the number of loading by using the aforementioned X-ray diffraction ring. A curved line in each figure indicates a relation between the number of loading and each use condition element calculated based on data points in the figure.

Namely, when the X-rays are emitted onto the bearing part (bearing part 90 to be inspected) forming the rolling bearing after use in the aforementioned step (S20) and the bearing part is analyzed by using the entire X-ray diffraction ring detected in the step (S40), analytical values corresponding to the horizontal axes in FIGS. 4 to 6 are obtained, and thus, the highest possible number of loading can be derived from these analytical values by using the relations shown in FIGS. 4 to 6. More specifically, referring to FIG. 7, assuming that the compressive stress of bearing part 90 to be inspected which was obtained from the X-ray diffraction ring is, for example, x, the number of loading can be estimated as y. Similarly, by preliminarily researching a relation between the compressive stress or the other use condition elements and the other use condition (the load, the oil film parameter), the other use condition of bearing part 90 to be inspected can be derived (estimated) by using this relation.

Assuming now that the compressive stress of bearing part 90 to be inspected is x, the probability that the number of loading is y is the highest, judging from only this data. However, the number of loading calculated as described above includes variations in analysis result and variations caused by the other use condition (the load, the oil film parameter).

Figure 7:
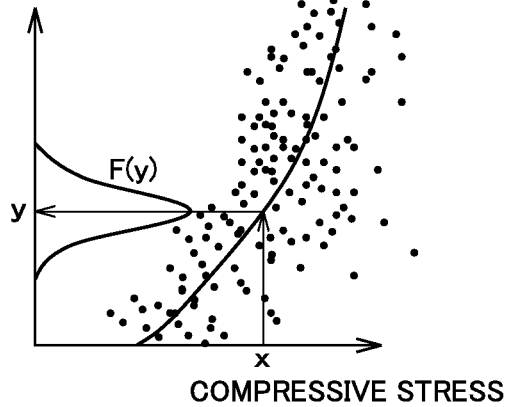
FIG. 7 is a diagram for describing a procedure for deriving the number of loading.

As shown in FIG. 7, the number of loading has a distribution like F(y) with respect to the compressive stress. Similarly, the number of loading has distributions with respect to all use condition elements (such as the half-value width corresponding to a certain central angle, and the peak intensity corresponding to a certain central angle). Therefore, by multiplying all of these distribution functions and determining at which number of loading the multiplied functions are maximized, the most likely number of loading can be derived. Therefore, when the number of loading is derived, it is preferable to multiply, as many as possible, the distribution functions for the number of loading derived based on relations between the number of loading and the respective use condition elements that are preliminarily researched, and to derive the most likely number of loading. More specifically, it is preferable to multiply all distribution functions for the number of loading derived based on, for example, a relation of the number of loading with each of the normal stress at the fatigued portion, the shear stress at the fatigued portion, the amount of remaining austenite, the relation between the central angle and the intensity of the annular diffracted X-rays, and the half-value width of the peak obtained in accordance with the central angle of the annular diffracted X-rays, about the preliminarily researched bearing part, and to statistically derive the most likely number of loading. Then, the most likely values of not only the number of loading but also the load and the oil film parameter are similarly derived statistically. As a result, the use condition can be estimated with high precision. The calculated use condition is displayed on display unit 14 connected to computation unit 13.

Next, referring to FIG. 3, a step of calculating the remaining life of the rolling bearing (S50) is performed. In this step (S50), the remaining life of bearing part 90 to be inspected is calculated based on the use condition derived in the aforementioned step (S40). Specifically, the remaining life can be estimated, for example, as described below.

Generally, the life of the rolling bearing is expressed by the following equation (1):

$$L_n = a_1 a_2 \left(\frac{C}{P}\right)^p \quad (1)$$

where $$a_1 = \left(\frac{\ln(1-0.01n)}{\ln 0.9}\right)^{1/e} \text{ or } a_1 = \left\{0.95\left(\frac{\ln(1-0.01n)}{\ln 0.9}\right)^{1/e} + 0.05\right\}$$

$L_n$: n % life (the number of loading), $a_1$: reliability coefficient, $a_2$: use condition coefficient (coefficient determined by use condition such as lubrication condition), P: load (kgf), C: dynamic load rating (kgf), p: load life exponent (ball bearing: p=3, roller bearing: p=10/3), e: Weibull slope (ball bearing: e=10/9, roller bearing: e=9/8) (e=1.5 in the case of 10% life or less).

Therefore, by applying the use condition (the number of loading, the load and the oil film parameter) derived in the aforementioned step (S40) to the aforementioned equation (1), the remaining life of bearing part 90 to be inspected is calculated. The calculated remaining life is displayed on display unit 14. With the aforementioned process, the inspection method for the bearing part using inspection apparatus 1 according to the present embodiment is completed.

In the aforementioned inspection method for the bearing part using inspection apparatus 1 or 2 according to the present embodiment, the use condition of the bearing part such as a bearing ring and a rolling element that forms the rolling bearing is calculated based on the X-ray diffraction ring in which the amount of information obtained in one measurement is significantly larger than that in the conventional method. Therefore, the use condition of the rolling bearing (bearing part) is estimated with high precision.

In the aforementioned embodiment, the maximum likelihood estimation method has been described as one example of the statistical method for estimating the use condition. However, instead of this method, other statistical methods, e.g., a Bayesian method may be used.

It should be understood that the embodiment disclosed herein is illustrative and not limitative in any respect. The scope of the present invention is defined by the terms of the claims, rather than the description above, and is intended to include any modifications within the scope and meaning equivalent to the terms of the claims.

INDUSTRIAL APPLICABILITY

The inspection method for the bearing part and the inspection apparatus for the bearing part according to the present invention are particularly advantageously applicable to an inspection method for a bearing part and an inspection apparatus for a bearing part in which high precision is required.

REFERENCE SIGNS LIST

1, 2 inspection apparatus, 11 irradiation unit, 12 detector; 12A detection unit; 12B imaging plate; 12C table; 13 computation unit, 14 display unit, 21 first device, 22 second device, 90 bearing part to be inspected, 120 read unit; 121 first motor, 122 second motor; 123 table; 124 laser beam irradiation device; 125 calculation circuit.

The invention claimed is:

1. An inspection method for a bearing part, comprising the steps of:
    emitting X-rays onto a fatigued portion of a bearing part to be inspected; detecting annular diffracted X-rays diffracted by said fatigued portion;
    deriving one or more use condition elements based on the detected annular diffracted X-rays, wherein the one or more use condition elements include normal stress at said fatigued portion, shear stress at said fatigued portion, a relation between a central angle and an intensity of said annular diffracted X-rays, a half-value width of a peak obtained in accordance with the central angle of said annular diffracted X-rays, and an amount of austenite remaining in said fatigued portion; and
    estimating a one or more use conditions of said bearing part, by statistical calculation based on known relationships between the respective use conditions and each of the one or more use condition elements, wherein the one or more use condition include the number of loading of stress applied to said fatigued portion of said bearing part to be inspected, a load applied to said fatigued portion, and an oil film parameter at said fatigued portion;
    estimating a remaining life for the bearing part based on the use condition.

2. An inspection apparatus for a bearing part, comprising:
    an irradiation unit for emitting X-rays onto a bearing part to be inspected;
    a detector for detecting annular X-rays diffracted by said bearing part to be inspected; and
    a computation unit connected to said detector, configured to:
        derive one or more use condition elements based on the detected annular diffracted X-rays,
        estimate one or more use conditions of said bearing part, by statistical calculation based on known relationships between the respective use conditions and each of the derived one or more use condition elements
        estimate a remaining life for the bearing part based on the estimated use condition; and a display configured to display the estimated remaining life for the bearing part.

3. The inspection apparatus for a bearing part according to claim 2, wherein
    the inspection apparatus for a bearing part is portable.

* * * * *